(12) United States Patent
Chen et al.

(10) Patent No.: US 6,720,001 B2
(45) Date of Patent: *Apr. 13, 2004

(54) EMULSION COMPOSITIONS FOR POLYFUNCTIONAL ACTIVE INGREDIENTS

(75) Inventors: Feng-Jing Chen, Salt Lake City, UT (US); Mahesh V. Patel, Salt Lake City, UT (US)

(73) Assignee: Lipocine, Inc., Salt Lake City, UT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/420,159

(22) Filed: Oct. 18, 1999

(65) Prior Publication Data

US 2002/0107265 A1 Aug. 8, 2002

(51) Int. Cl.$^7$ .......... A61K 9/127; A61K 9/48; A61K 9/66
(52) U.S. Cl. ......... 424/455; 424/450; 424/456; 424/400
(58) Field of Search .............. 514/937, 570, 514/458; 424/45, 400, 450, 451, 455

(56) References Cited

U.S. PATENT DOCUMENTS

| | | | | |
|---|---|---|---|---|
| 4,711,902 A | | 12/1987 | Serno | 514/356 |
| 4,719,239 A | | 1/1988 | Muller et al. | 514/785 |
| 4,753,963 A | * | 6/1988 | Jandacek et al. | 514/552 |
| 4,816,247 A | | 3/1989 | Desai et al. | 424/80 |
| 4,871,768 A | * | 10/1989 | Bistrian et al. | 514/547 |
| 4,990,337 A | | 2/1991 | Kurihara et al. | 424/427 |
| 5,098,606 A | | 3/1992 | Nakajima et al. | 252/358 |
| 5,342,625 A | * | 8/1994 | Hauer et al. | 424/455 |
| 5,364,632 A | | 11/1994 | Benita et al. | 424/450 |
| 5,407,683 A | | 4/1995 | Shively | 424/439 |
| 5,527,537 A | | 6/1996 | Dietl | 424/450 |
| 5,534,261 A | * | 7/1996 | Rodgers et al. | 424/450 |
| 5,616,330 A | | 4/1997 | Kaufman et al. | 424/400 |
| 5,616,332 A | * | 4/1997 | Herstein | 424/401 |
| 5,616,342 A | | 4/1997 | Lyons | 424/450 |
| 5,622,714 A | | 4/1997 | Dietl | 424/450 |
| 5,660,858 A | | 8/1997 | Parikh et al. | 424/450 |
| 5,661,180 A | * | 8/1997 | DeMichele et al. | 514/547 |
| 5,681,855 A | | 10/1997 | Schütz et al. | 514/559 |
| 5,693,337 A | | 12/1997 | Suzuki et al. | 424/450 |
| 5,698,593 A | * | 12/1997 | Peck | 514/557 |
| 5,731,355 A | | 3/1998 | Jones et al. | 514/731 |
| 5,780,676 A | * | 7/1998 | Boehm et al. | 562/490 |
| 6,013,665 A | * | 1/2000 | DeMichele et al. | 514/458 |
| 6,030,374 A | * | 2/2000 | McDaniel | 604/506 |
| 6,130,244 A | * | 10/2000 | DeMichele et al. | 514/474 |
| 6,160,007 A | * | 12/2000 | DeMichele et al. | 514/458 |
| 6,267,985 B1 | * | 7/2001 | Chen et al. | 424/451 |
| 6,294,192 B1 | * | 9/2001 | Patel et al. | 424/451 |
| 6,309,663 B1 | * | 10/2001 | Patel et al. | 424/450 |
| 6,316,497 B1 | * | 11/2001 | Liu et al. | 514/475 |
| 6,320,074 B1 | * | 11/2001 | Boehm et al. | 562/490 |
| 6,333,999 B1 | * | 12/2001 | Brownsmith | 382/229 |
| 6,339,107 B1 | * | 1/2002 | Belloni | 514/725 |
| 6,451,339 B2 | * | 9/2002 | Patel et al. | 424/451 |
| 2001/0025046 A1 | * | 9/2001 | LIU et al. | 514/310 |
| 2003/0133974 A1 | * | 7/2003 | Curatolo et al. | 424/456 |

FOREIGN PATENT DOCUMENTS

| | | | |
|---|---|---|---|
| WO | 89/02275 | * | 3/1989 |
| WO | 94/08603 | * | 4/1994 |
| WO | 95/31110 | * | 11/1995 |
| WO | 97/25977 | * | 7/1997 |

OTHER PUBLICATIONS

Lucero et al., Therapeutic efficacy . . . , abstract, Internationak Journal of Pharmaceutics, 1996, vol. 127(1), pp. 73–83.*
Babayan, V.K., "Medium Chain Triglycerides and Structured Lipids," Specialty Lipids and Their Biofunctionality Symposium, *LIPIDS*, vol. 22, No. 6 (1987).
www.rxmed.com/monographs/diazem.html, publication date unknown.

* cited by examiner

*Primary Examiner*—Vickie Kim
(74) *Attorney, Agent, or Firm*—Thorpe, North & Western, LLP

(57) ABSTRACT

The present invention provides pharmaceutical oil-in-water emulsions for delivery of polyfunctional active ingredients. The emulsions include an aqueous phase, an emulsifier, and an oil phase, wherein the oil phase includes a structured triglyceride that is substantially free of triglycerides having three $C_6$–$C_{12}$ fatty acid moieties, or a combination of a long chain triglyceride and a polarity-enhancing polarity modifier. The present invention also provides methods of treating an animal with a polyfunctional active ingredient, using dosage forms of the pharmaceutical emulsions.

21 Claims, No Drawings

US 6,720,001 B2

EMULSION COMPOSITIONS FOR POLYFUNCTIONAL ACTIVE INGREDIENTS

FIELD OF THE INVENTION

The present invention relates to pharmaceutical delivery systems, and in particular to oil-in-water pharmaceutical emulsions for the improved delivery of polyfunctional active ingredients, such as pharmaceuticals, cosmeceuticals, nutritive agents, and diagnostic agents.

BACKGROUND

Polyfunctional active ingredients, i.e., active ingredients having at least some polar functionality, present difficult problems in formulating such compounds for effective administration to patients. A well-designed formulation should, at a minimum, be capable of presenting a therapeutically effective amount of the polyfunctional compound to the desired site of action, in a bioavailable form. Particularly when the polyfunctional active ingredient is hydrophobic, this minimal functionality has proven difficult to achieve. Delivery of a polyfunctional hydrophobic active ingredient requires interaction with aqueous physiological environments, such as blood, gastric fluids and intestinal fluids. Pharmaceutical compositions for delivery of such polyfunctional hydrophobic active ingredients should preferably carry the active ingredient through the aqueous environment, while maintaining the active ingredient compound in a bioavailable form, and avoiding or substantially reducing the use of physiologically harmful solvents or excipients.

A number of approaches to formulating polyfunctional hydrophobic active ingredients for oral or parenteral delivery are known. Several commercial formulations are available for parenteral dosage forms of polyfunctional active ingredients, based on organic cosolvent and/or synthetic surfactant solvent systems. For example, cyclosporin A (SANDIMMUNE®), paclitaxel (TAXOL®) and etoposide (VePesid®) are all commercially available in injectable dosage forms containing organic solvents and/or synthetic hydrophilic surfactants. See, *Physician's Desk Reference*, Medical Economics Co. (1999).

Solvent/hydrophilic surfactant formulations, however, suffer from a number of serious disadvantages. Hydrophilic polyethoxylated surfactants commonly used in such formulations, such as Cremophor® and Tween®, have a high toxicity potential. Pain at the injection site, thrombophlebitis, tissue necrosis and hypersensitivity reactions are commonly observed side effects of such formulations. Cremophor EL, for example, currently used in parenteral formulations of cyclosporin, paclitaxel and teniposide, has been found to be associated with severe anaphylactic/hypersensitive reactions. Cremophor EL has also been implicated at least partially responsible in the most significant side effect of cyclosporin concentrate for injection, acute nephrotoxicity. Besides being irritating and hemolytic, such formulations are potentially subject to active precipitation during storage, upon admixing prior to administration, or upon parenteral administration, leading to further safety challenges. In addition, some hydrophilic polyethoxylated surfactants, such as Cremophor EL, cause phthalate stripping and are incompatible with commonly used plasticized PVC infusion devices.

As an alternative to hydrophilic surfactant/cosolvent systems, oil-in-water ("o/w") emulsion formulations have been used in polyfunctional hydrophobic active ingredient delivery. These formulations typically contain a long chain triglyceride oil phase dispersed in water and stabilized by an emulsifier layer of a phosphatide, such as soy or egg lecithin. Propofol, for example, is available commercially as Diprivan®, an o/w emulsion formulation using long chain triglycerides contained in vegetable oils, and an emulsifying agent. While such formulations may overcome some of the safety liabilities of hydrophilic surfactant/solvent based systems, the oil component may not be appropriately polar to effectively incorporate polyfunctional active ingredients at desirable therapeutic levels, without compromising product safety.

In an attempt to improve drug loading capacity in emulsions, some approaches incorporate additional stabilizers, or include undesirably high levels of compounds which hydrolyze to form medium chain fatty acids. Such approaches, however, present problems in processing, stability, and safety.

Several formulations have been developed based on medium chain triglyceride ("MCT") oil phases, rather than (or in addition to) the more traditional long chain triglyceride ("LCT") oil phases. U.S. Pat. No. 5,660,858 to Parikh et al. discloses cyclosporin oil-in-water emulsions with a synthetic MCT having predominantly $C_8$–$C_{12}$ fatty acid chains. U.S. Pat. No. 5,364,632 to Benita et al. discloses an oil-in-water emulsion of a lipophilic drug having an MCT oil carrier and a combination of ionic and non-ionic surfactants.

Reportedly, such formulations enable better solubilization of polyfunctional active ingredients, compared to the less polar long chain triglycerides. See, e.g., Velazquez et al, "The scientific rationale and clinical application of short-chain fatty acids and medium-chain triglycerides," *Proceedings of the Nutrition Society*, 55:49–78 (1996). However, the presence of predominantly medium chain (i.e., having fatty acids with carbon chain lengths of six to ten carbon atoms) triglycerides of higher polarity in the oil phase presents significant safety and stability issues that could limit the shelf live of MCT-based formulations, or place safety limits on the infusion rate. See, Velazquez et al., ibid, and Van de Velde et al., "Comparative hemodynamic effects of three different parenterally administered lipid emulsions in conscious dogs," *Crit. Care Med.*, 26:132–137 (1998).

The adverse effects of parenteral MCT-based emulsions reported in animals include poor growth and nitrogen balance, and increased energy expenditure. Some reports have indicated that medium chain triglycerides may not spare protein catabolism as well as do long chain triglycerides. More importantly, MCT-based emulsions do not seem to be well-tolerated by patients. Moderate to severe side effects have been reported, such as neurotoxicity, emesis, somnolence, coma, narcosis, essential fatty acid deficiency, and ketosis in susceptible patients. Since physical mixing of MCTs and LCTs does not alter the subsequent clearance kinetics, the corresponding triacyl glycerols are cleared from the blood and oxidized unaffected in the mixture. As a result, very rapid hydrolysis of MCTs and rapid uptake of the medium chain fatty acid hydrolysis products have been observed even in a one-to-one mixture of MCTs and LCTs administered parenterally. Some of the reported side effects have been attributed to uncoupling of oxidative phosphorylation resulting from the uncontrolled entry of medium chain fatty acids into the mitochondria, due to the rapid hydrolysis of MCTs.

As a specific example, caprylic acid, the hydrolysis product of an MCT containing the caprylic acid ester moiety, has been demonstrated to have neurological side effects.

Caprylic acid infusion simultaneously produced alterations in the sodium-potassium-adenosinetriphosphatase activity in brain tissue, and resulted in hyperventilation, coma, seizure, hypotonia and electroencaphalographic changes in rabbits. (Velazquez et al., *Proceedings of the Nutrition Society*, 55:49–78 (1996)). These events coincide with hemodynamic events, such as a decrease in cardiac output, stroke volume, and myocardial wall-thickening fraction, and an increase in aortic blood pressure and systemic vascular resistance when an MCT/LCT mixture is infused parentally in dogs. (Van de Velde et al., *Crit. Care Med.*, 26:132–137 (1998)). Thus, medium chain triglycerides and medium-chain-containing additives, such as medium chain mono- or diglycerides, which hydrolyze to medium chain fatty acids, present potentially severe safety problems in pharmaceutical emulsions.

Thus, there is a need for safe and effective pharmaceutical formulations of polyfunctional active ingredients that do not suffer from the foregoing disadvantages.

SUMMARY OF THE INVENTION

It is an object of the invention to provide pharmaceutical delivery systems capable of delivering polyfunctional active ingredients.

It is another object of the invention to provide pharmaceutical emulsions for delivery of polyfunctional active ingredients with improved loading capacity.

It is another object of the invention to provide pharmaceutical emulsions for delivery of polyfunctional active ingredients that are substantially free of toxic hydrophilic surfactants.

It is another object of the invention to provide pharmaceutical emulsions for delivery of polyfunctional active ingredients which reduce irritation and local toxicity at the site of administration.

It is another object of the invention to provide pharmaceutical emulsions for delivery of polyfunctional active ingredients which overcome drug precipitation upon administration.

It is another object of the invention to provide pharmaceutical emulsions for delivery of polyfunctional active ingredients with fewer side effects associated with medium chain triglycerides or their hydrolysis products.

It is another object of the invention to provide pharmaceutical emulsions for delivery of polyfunctional active ingredients with enhanced stability.

It is another object of the invention to provide safer and more effective methods of treatment with polyfunctional active ingredients.

In accordance with these and other objects, the present invention provides pharmaceutical emulsions and methods utilizing the emulsions, to provide improved delivery of polyfunctional active ingredients. The pharmaceutical emulsions of the present invention include an aqueous phase, an oil phase, and an emulsifier, wherein the oil phase includes components chosen to increase the polarity of the oil phase, without introducing into the emulsion excessive amounts of organic solvents, hydrophilic surfactants, or compounds which include or hydrolyze to form medium chain fatty acids.

In one embodiment, the present invention provides a pharmaceutical emulsion for delivery of a polyfunctional active ingredient, the emulsion including an aqueous phase, an emulsifier, and a polar oil phase containing one or more structured triglycerides. The structured triglyceride can include both medium and long chain fatty acids, and is preferably free of triglycerides having three medium chain fatty acid moieties. Optionally, the composition can include additional components, such as a polyfunctional active ingredient, a long chain triglyceride, a polarity modifier, ingredients to facilitate formulation stability and patient acceptability, and processing aids.

In another embodiment, the present invention provides a pharmaceutical emulsion for delivery of a polyfunctional active ingredient, the emulsion including an aqueous phase, an emulsifier, and an oil phase containing a long chain triglyceride and at least one compound selected from the group consisting of acids; bases; monoglycerides; diglycerides; mixtures of mono- and diglycerides; mixtures of mono-, di- and triglycerides, acetylated monoglycerides; acetylated diglycerides; bile acids; cholesterol; cholesterol fatty acid esters; fatty acids; fatty alcohols; fusidic acids; lactic acid derivatives of mono/diglycerides; lower alcohol fatty acid esters; propylene glycol fatty acid esters; polyol fatty acid esters; polyol alkyl ethers; lipophilic reaction mixtures of polyols and at least one member of the group consisting of fatty acids, glycerides, vegetable oils, hydrogenated vegetable oils, and sterols; sorbitan fatty acid esters; polyethoxylated esters; polyethoxylated alkyl ethers; and polyethoxylated sterols. Optionally, the composition can include additional components, such as a polyfunctional active ingredient, a structured triglyceride, a mono- or diglyceride, an acid or base, ingredients to facilitate formulation stability and patient acceptability, and processing aids.

In another embodiment, the present invention provides a pharmaceutical emulsion for delivery of a polyfunctional active ingredient, the emulsion including an aqueous phase, an emulsifier, and an oil phase containing a long chain triglyceride and a monoglyceride, a diglyceride, a mixture of mono- and diglycerides, or a mixture of mono-, di- and triglycerides. Optionally, the composition can include additional components, such as a polyfunctional active ingredient, a structured triglyceride, a polarity modifier, ingredients to facilitate formulation stability and patient acceptability, and processing aids.

In another embodiment, the present invention provides a pharmaceutical emulsion for delivery of a polyfunctional active ingredient, the emulsion including an aqueous phase, an emulsifier, and an oil phase containing a long chain triglyceride and an acetylated monoglyceride, an acetylated diglyceride, or a mixture thereof. Optionally, the composition can include additional components, such as a polyfunctional active ingredient, a structured triglyceride, a polarity modifier, ingredients to facilitate formulation stability and patient acceptability, and processing aids.

In another embodiment, the present invention provides dosage forms of the pharmaceutical emulsions.

In another aspect, the present invention relates to methods of using the pharmaceutical emulsions to treat patients with a polyfunctional active ingredient.

In another aspect, the present invention relates to methods of treating a patient with a pharmaceutical composition, wherein the composition includes effective amounts of an oil phase and an emulsifier. The amounts and components of the oil phase and emulsifier are effective to minimize drug precipitation upon administration, irritation and local toxicity at the site of administration; to alter drug biodistribution and clearance; and to minimize systemic drug toxicity, multi-drug resistance, intra-subject performance variability and/or inter-subject performance variability.

These and other objects and features of the present invention will become more fully apparent from the following description and appended claims, or may be learned by the practice of the invention as set forth hereinafter.

DETAILED DESCRIPTION OF THE PREFERRED EMBODIMENTS

The present invention provides pharmaceutical emulsions and methods utilizing the emulsions, to provide improved delivery of polyfunctional active ingredients, particularly hydrophobic polyfunctional active ingredients. Unlike conventional formulations, the pharmaceutical emulsions of the present invention achieve effective and stable solubilization of the polyfunctional active ingredient without excessive amounts of organic solvents, hydrophilic synthetic surfactants, or medium chain fatty acid containing compounds, such as medium chain triglycerides. The pharmaceutical emulsions of the present invention include an aqueous phase, an oil phase, and an emulsifier, wherein the oil phase includes safe and effective components chosen to increase the polarity of the oil phase, while maintaining formulation safety and stability.

In one embodiment, the oil phase includes a structured triglyceride. The term "structured triglyceride" as used herein means a triglyceride, or a mixture of triglycerides, of synthetic or natural origin, having a fatty acid chain composition including both medium chain fatty acids and long chain fatty acids. Conventional oils, such as vegetable oils, are primarily composed of triglycerides of long chain fatty acids. In contrast, MCT oils are synthetic oils primarily composed of triglycerides of $C_8$–$C_{10}$ fatty acids. As used herein, the term "medium chain fatty acid" means a saturated or unsaturated fatty acid having a carbon chain length of 6 to 12 carbon atoms, whereas the term "long chain fatty acid" means a saturated or unsaturated fatty acid having a carbon chain length of greater than 12 carbon atoms. Typical long chain and medium chain triglycerides can be characterized by their fatty acid content, reported in one literature source as follows:

| Fatty Acid | Soybean Oil | Safflower Oil | MCT Oil |
|---|---|---|---|
| C6 | | | <2% |
| C8 | | | 70% |
| C10 | | | 30% |
| C12 | | | <2% |
| C14 | 0.1% | 0.1% | |
| C16 | 10.5% | 6.7% | |
| C18 | 88.5% | 93.1% | |
| C20 | 1.1% | 1.0% | |

(Babayan, *Lipids*, 22(6):417–420 (1987); different degrees of saturation combined).

In contrast to both medium chain and long chain triglycerides, structured triglycerides include both medium chain and long chain fatty acid groups. Structured triglycerides are typically synthetically produced, and are typically a mixture of triglycerides having predominantly medium and long chain fatty acid groups. An example of commercially available structured triglycerides is the Captex 810 series (Abitec), which is reported to have the following fatty acid distribution:

| Fatty Acid Chain Distribution | 810A | 810B | 810C | 810D |
|---|---|---|---|---|
| 3 medium | 62 | 39 | 15 | 3 |
| 2 medium 1 long | 32 | 43 | 40 | 20 |
| 1 medium 2 long | 6 | 16 | 27 | 44 |
| 3 long | <1 | 2 | 3 | 34 |

(Babayan, ibid.) In order to avoid the adverse effects of MCT oils and their hydrolysis products, preferably the structured triglyceride does not contain significant amounts of triglycerides having three medium chain fatty acid groups. Thus, preferred structured triglycerides are those which are substantially free of MCTs, such as Captex 810D. Alternatively, fractions of Captex 810A or similar compositions which are substantially free of triglycerides having three medium chain fatty acid groups, obtained by appropriate procedures, are also suitable for use in the emulsion compositions of the present invention.

Structured triglycerides can be produced by various methods known in the art, including hydrolysis and esterification; interesterification; traditional chemical reaction sequences; lipase interesterification; genetic manipulation; or other methods, as appropriate.

Mixtures of long chain triglycerides and structured triglycerides are also within the scope of the present invention. In this embodiment, the oil phase can further include one or more oils having long chain triglycerides, such as vegetable oils, fish oils, animal fats, hydrogenated vegetable oils, partially hydrogenated vegetable oils, semi-synthetic triglycerides, synthetic triglycerides, or mixtures thereof. Fractionated, refined or purified oils of these types can also be used.

Specific examples of suitable long chain triglyceride-containing oils suitable for use in the compositions of the present invention include almond oil; babassu oil; borage oil; black currant seed oil; canola oil; castor oil; coconut oil; corn oil; cottonseed oil; emu oil; evening primrose oil; flax seed oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; a mixture of hydrogenated cottonseed oil and hydrogenated castor oil; partially hydrogenated soybean oil; a mixture of partially hydrogenated soybean oil and partially hydrogenated cottonseed oil; glyceryl trioleate; glyceryl trilinoleate; glyceryl trilinolenate; a Ω3 polyunsaturated fatty acid triglyceride containing oil; and mixtures thereof.

Preferred long chain triglyceride containing oils include coconut oil; corn oil; olive oil; palm oil; peanut oil; safflower oil; sesame oil; soybean oil; hydrogenated castor oil; hydrogenated coconut oil; partially hydrogenated soybean oil; glyceryl trioleate; glyceryl trilinoleate; glyceryl trilinolenate; Ω3 polyunsaturated fatty acid triglyceride containing oil; and mixtures thereof.

More preferred long chain triglyceride containing oils include corn oil; olive oil; palm oil; peanut oil; safflower oil; sesame oil; soybean oil; hydrogenated castor oil; partially hydrogenated soybean oil; glyceryl trioleate; glyceryl trilinoleate; a Ω3 polyunsaturated fatty acid triglyceride containing oil; and mixtures thereof.

The oil phase can further include one or more polarity modifiers. Without wishing to be bound by theory, it is believed that these polarity modifiers can act as polarity enhancers, to assist in adjusting the polarity of the oil phase to maximize the beneficial properties of the present emulsions. The polarity modifier is a compound or a mixture of compounds, capable of modifying the interaction between the polyfunctional active ingredient and the oil phase by serving as a bridge to reduce the effects of the gap in polarity between the active ingredient and the oil.

Without wishing to be bound by theory, it is believed that the presence of a polarity modifier in the oil phase creates a more favorable environment for a polyfunctional active ingredient through interaction with the polarity modifier. These interactions may include hydrogen bonds, ion-dipole interactions, ion-induced dipole interactions, electrostatic interactions, and van der Waals forces, including dipole-dipole interactions (also known as Keesom forces), dipole-induced-dipole interactions (also known as Debye forces), and induced dipole-induced dipole interactions (also known as London dispersion forces).

These interactions can be in such a way that the incorporation of the polyfunctional active into the emulsion formulation is facilitated, or the behavior of the active upon administration is augmented in the presence of the emulsion formulation.

Suitable polarity modifiers include acids; bases; monoglycerides; diglycerides; mixtures of mono- and diglycerides; mixtures of mono-, di- and triglycerides; acetylated monoglycerides; acetylated diglycerides; bile acids; cholesterol; cholesterol fatty acid esters; fatty acids; fatty alcohols; fusidic acids; lactic acid derivatives of mono/diglycerides; lower alcohol fatty acid esters; propylene glycol fatty acid esters; polyol fatty acid esters; polyol alkyl ethers; sorbitan fatty acid esters; polyethoxylated esters; polyethoxylated alkyl ethers; polyethoxylated sterols; and mixtures thereof.

Other suitable polarity modifiers include lipophilic reaction mixtures, or purified/fractionated lipophilic reaction mixtures, of polyols and fatty acids, glycerides, vegetable oils, hydrogenated vegetable oils, or sterols. The glyceride can be a monoglyceride, a diglyceride, a triglyceride, or a mixture thereof.

It will be apparent to those skilled in the art that the term "lipophilic" means those members of the foregoing groups or classes of compounds which have significant solubility in oily solvents, and poor solubility in aqueous solvents. For compounds that can be characterized by a hydrophilic-lipophilic balance ("HLB") number, such as non-ionic compounds, lipophilic compounds are generally those having an HLB value of less than about 10.

A preferred lipophilic reaction mixture is the reaction mixture of a transesterification reaction of a polyol and a fatty acid, a glyceride, a vegetable oil, a hydrogenated vegetable oil, a sterol, or a mixture thereof.

Preferred lipophilic reaction mixtures are those in which the polyol reactant is a polyhydric aliphatic alcohol, such as pentaerythritol, ethylene glycol, polyethylene glycol, propylene glycol, polypropylene glycol, sorbitol, glycerol, polyglycerol, a saccharide, a cyclodextrin, a synthetic polyhydric polymer, or a mixture thereof.

Preferred polarity modifiers include monoglycerides; diglycerides; mixtures of mono- and diglycerides; mixtures of mono-, di- and triglycerides; acetylated monoglycerides; acetylated diglycerides; cholesterol fatty acid esters; lower alcohol fatty acid esters; propylene glycol fatty acid esters; polyol fatty acid esters; sorbitan fatty acid esters; polyethoxylated esters; polyethoxylated sterols; lipophilic reaction mixtures of polyols and fatty acids, glycerides, vegetable oils, hydrogenated vegetable oils, and sterols; and mixtures thereof.

Particularly preferred polarity modifiers are monoglycerides, diglycerides, mixtures of mono- and diglycerides. The monoglycerides and diglycerides preferably have fatty acids with carbon chain lengths of greater than 10 carbon atoms.

Also particularly preferred are acetylated monoglycerides, acetylated diglycerides, and mixtures thereof.

Other particularly preferred polarity modifiers include sorbitan fatty acid esters; polyethoxylated esters; polyethoxylated sterols; lipophilic reaction mixtures of polyols and at least one member of the group consisting of fatty acids, glycerides, vegetable oils, hydrogenated vegetable oils, and sterols; and mixtures thereof.

Still other preferred polarity modifiers include polyethoxylated esters, such as polyethoxylated monoglycerides, polyethoxylated diglycerides, polyethoxylated triglycerides, polyethoxylated bile acids, polyethoxylated cholesterol, polyethoxylated fatty acids, polyethoxylated propylene glycol esters, polyethoxylated vegetable oils, polyethoxylated hydrogenated vegetable oils, polyethoxylated sorbitan fatty acid esters, and mixtures thereof.

Suitable acids and bases are pharmaceutically acceptable acids and bases, preferably those which are oil-miscible, or which can interact with the polyfunctional active ingredient to bring the active and/or the acid or base into the oil phase. The acid can be an inorganic acid, an aliphatic acid, an aromatic acid, an acidic salt, or a mixture thereof. Examples of suitable acids include hydrochloric acid, hydrobromic acid, hydroiodic acid, sulfuric acid, carbonic acid, nitric acid, boric acid, phosphoric acid, acetic acid, acrylic acid, adipic acid, alginic acid, alkanesulfonic acid, an amino acid, ascorbic acid, benzoic acid, boric acid, butyric acid, carbonic acid, cinnamic acid, citric acid, fatty acids, formic acid, fumaric acid, gluconic acid, hydroquinosulfonic acid, hydroxybenzoic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, acidic salts of pharmaceutically acceptable cations and anions, and mixtures thereof.

The base can be an inorganic base, an aliphatic base, an aromatic base, a basic salt, or a mixture thereof. Examples of suitable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, glucamine and homologs thereof, diisopropylethylamine, ethanolamine, ethylenediamine, triethanolamine, triethylamine, trihydroxyethylamine, triisopropanolamine, basic salts of pharmaceutically acceptable cations and anions, and mixtures thereof.

The optional acids and bases can be included in amounts sufficient to adjust the pH and/or the osmolality of the emulsion, the solubility of the polyfunctional active ingredient, the kinetic release profile, or other properties of the emulsion, as desired.

In order to fully realize the important safety, stability, and other advantages of the compositions of the present invention, it is preferred that the total amount of fatty acid groups of the oil phase, including free fatty acids and the fatty acid moieties of fatty acid containing compounds, having a carbon chain length of from 6 to 12 carbon atoms, be less than about 50% by weight, preferably less than about 40% by weight, and more preferably less than about 30% by weight, based on the total weight of the fatty acid groups of the oil phase. Similarly, it is preferred that the total amount of fatty acid groups of the oil phase, including free fatty acids and the fatty acid moieties of fatty acid containing compounds, having a carbon chain length of greater than 12 carbon atoms, be greater than about 10% by weight, preferably greater than about 30% by weight, and more preferably greater than about 50% by weight, based on the total weight of the fatty acid groups of the oil phase.

The oil phase itself can be up to about 30% of the total weight of the emulsion, more typically up to about 20% of the total weight of the emulsion, and most typically up to about 10% of the total weight of the emulsion The pharmaceutical emulsions of the present invention also include an emulsifier in an amount sufficient to form an oil in water emulsion. It should be appreciated that the appropriate amount of emulsifier may be different, depending upon whether or not a polyfunctional active ingredient is present in the emulsion, since some active ingredients may have self-emulsifying properties, or may become self-emulsifying after interacting with certain polarity modifiers. The emulsifier stabilizes the emulsion by increasing the mechanical bilayer strength, and/or by charge repulsion and/or steric hindrance modifications. Typically, the emulsifier will be present in an amount of less than about 20% by weight, more typically less than about 10% by weight, based on the total weight of the composition. A suitable emulsifier can be ceramide; a mixed chain phospholipid; a cationic lipid; an oligolipid; a phospholipid; a carnitine; a sphingosine; a sphigomyelin; a glycolipid; a lipoprotein; an apoprotein; an amphiphilic protein/peptide; an amphiphilic synthetic polymer; a bile salt; a fatty acid; a fatty alcohol; a fatty amine; a fatty quaternary ammonium salt; a polyethoxylated fatty acid; a polyethoxylated glyceride; a polyethoxylated phospholipid; a polyethoxylated sorbitan fatty acid ester; a polyethoxylated sterol; a polyethoxylated vegetable oil; a polyethoxylated hydrogenated vegetable oil; a reaction mixture of a polyol and at least one member of the group consisting of fatty acids, glycerides, vegetable oils, hydrogenated vegetable oils, and sterols; a sorbitan fatty acid ester; or a mixture thereof.

The glyceride of the reaction mixture can be a monoglyceride, a diglyceride, a triglyceride, or a mixture thereof. The polyol of the reaction mixture is preferably a polyhydric aliphatic alcohol, such as pentaerythritol, ethylene glycol, polyethylene glycol, propylene glycol, polypropylene glycol, sorbitol, glycerol, polyglycerol, a saccharide, a cyclodextrin, a synthetic polyhydric polymer, or a mixture thereof. The reaction mixture is preferably a reaction mixture of a transesterification reaction of a polyol and a fatty acid, a glycerides, a vegetable oil, a hydrogenated vegetable oil, a sterol, or a mixture thereof.

Preferred emulsifiers include phospholipids, such as egg phospholipids, soy phospholipids, phosphatidylcholines, phosphatidylethanolamines, phosphatidylserines, phophatidylglycerols, phosphatidylinositols, phosphatidic acids, mixed chain phospholipids, lysophospholipids, hydrogenated phospholipids, partially hydrogenated phospholipids, and mixtures thereof.

The emulsions of the present invention can also include other additives, such as glycerol, ethanol, propylene glycol, an antioxidant, an antiseptic, a buffering agent, a chelating agent, a colorant, a flavorant, an odorant, an osmotic modifier, a preservative, a solubilizer, a solvent, a tonicifier, a trace element, a viscomodulator, or a mixture thereof. Such additional additives can be present in the oil phase, the aqueous phase, or both.

Preferably, the pharmaceutical emulsion includes a polyfunctional active ingredient; i.e., an active ingredient having at least some polar functionality. Such active ingredients can be drugs, cosmeceuticals, nutritional agents, diagnostic agents and the like. In one embodiment, the polyfunctional active ingredient is a hydrophilic active ingredient having an octanol/water partition coefficient (i.e., the ratio of its activity in octanol to its activity in water) of less than about 100, preferably less than about 10. In another embodiment, the polyfunctional active ingredient is a hydrophobic active ingredient having an intrinsic aqueous solubility of less than about 1 mg/mL, preferably less than about 0.1 mg/mL. Of course, salts, isomers, derivatives, and mixtures of polyfunctional active ingredients can also be used.

Polyfunctional active ingredients can be, for example, analgesics and anti-inflammatory agents, anthelmintics, anti-arrhythmic agents, anti-asthma agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents and immunosuppressants, anti-protozoal agents, anti-thyroid agents, anti-tussives, anxiolytic, sedatives, hypnotics and neuroleptics, β-Blockers, cardiac inotropic agents, corticosteroids, diuretics, anti-parkinsonian agents, gastrointestinal agents, histamine $H_1$-receptor antagonists, keratolytics, lipid regulating agents, muscle relaxants, anti-anginal agents, sex hormones and stimulants,. The polyfunctional active ingredient can also be a cytokine, a peptidomimetic, a protein, a peptide, a toxoid, a serum, an antibody, a vaccine, a nucleoside, a nucleotide, a portion of genetic material, a nucleic acid, DNA, RNA, an oligodeoxynucleotide, or an oligonucleotide.

Examples of suitable polyfunctional active ingredients include acarbose; acyclovir; acetyl cysteine; acetylcholine chloride; alatrofloxacin; alendronate; alglucerase; amantadine hydrochloride; ambenomium; amifostine; amiloride hydrochloride; aminocaproic acid; amphotericin B; antihemophilic factor (human); antihemophilic factor (porcine); antihemophilic factor (recombinant); aprotinin; asparaginase; atenolol; atracurium besylate; atrophine; azithromycin; aztrconam; BCG vaccine; bacitracin; becaplermin; belladona; bepridil hydrochloride; bleomycin sulfate; calcitonin human; calcitonin salmon; carboplatin; capecitabine; capreomycin sulfate; cefamandole nafate; cefazolin sodium; cefepime hydrochloride: cefixime: cefonicid sodium; cefoperazone; cefoteran disodium: cefotaxime; cefoxitin sodium; ceftizoxime; cefhiaxone; cefuroxime axetil; cephalexin; cephapirin sodium; cholera vaccine; chorionic gonadotropin; cidofovir; cisplatin; cladribine; clidinium bromide; clindamycin and clindamycin; ciprofloxacin; clodronate; colistimethate sodium; colistin sulfate; corticotropin; cosyntropin; cromolyn sodium; cytarabine; dalteperin sodium; danaparoid; deferoxamine; denileukin diftitox; desmopressin; diatrizoate meglumine and diatrizoate sodium; dicyclomine; didanosine; dirithromycin; dopamine hydrochloride; dornase alpha; doxacurium chloride; doxorubicin; clidonate disodium; enalaprilat; enkephalin; enoxacin; enoxaparin sodium; ephedrine; epinephrine; epoetin alpha; erythromycin; esmolol hydrochloride; factor IX; famcilovir; fludarabine; fluoxetine; foscarnet sodium; ganciclovir; granulocyte colony stimulating factor; granulocyte-macrophage stimulating factor; recombinant human growth hormone; bovine growth hormone; gentamycin; glucagon; glycopyrolate; gonadotropin releasing hormone and synthetic analogs thereof; gonadorelin; grepafloxacin; haemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human; insulin lispro; insulin porcine; insulin NPII; insulin aspart; insulin glargine; insulin detemir; interferon alpha; interferon beta; ipratropium bromide; isophosphamide; Japanese encephalitis virus vaccine; lamivudine; leucovorin calcium leuprolide acetate; levofloxacin; lincomycin and lincomycin derivatives; lobucavir; lomefloxacin; loracarbef, mannitol; measles virus vaccine; meningococcal vaccine; menotropins; mepenzolate bromide; mesalamine; methenamine; methotrexate; methscopolamine; metformin hydrochloride; metoprolol; mezlocillin sodium; mivacurium chloride; mumps viral vaccine; nedocromil sodium; neostigmine bromide; neostigmine methyl sulfate; neurontin; norfloxacin; octreotide acetate; ofloxacin; olpadronate; oxytocin; pamidronate disodium; pancuronium bromide; paroxetine; pefloxacin; pentamidine isethionate; pentostatin; pentoxifylline; penciclovir; pentagastrin; phentolamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymyxin B sulfate; pralidoxime chloride; pramlintide; pregabalin; propafenone; propantheline bromide; pyridostigmine bromide; rabies vaccine; risedronate; ribavirin; rimantadine hydrochloride; rotavirus vaccine; salmeterol xinafoate; sincalide; small pox vaccine; sotalol; somatostatin; sparfloxacin; spectinomycin; stavudine; streptokinase; streptozocin; suxamethonium chloride; tacrine hydrochloride; terbutaline sulfate; thiotepa; ticarcillin; tiludronate; timolol; tissue type plasminogen activator; TNFR:Fe; TNK-tPA; trandolapril; trimetrexate gluconate; trospectomycin; trovafloxacin; tubocurarine chloride; tumor necrosis factor; typhoid vaccine live; urea; urokinase; vancomycin; valacyclovir; valsartan; varicella virus vaccine live; vasopressin; vecuronium bromide; vinblastine; vincristine; vinorelbine; warfarin sodium; yellow fever vaccine; zalcitabine; zanamivir; zolodronate; and zidovudine.

Additional examples of suitable polyfunctional active ingredients include tramadol, celecoxib, etodolac, rofecoxib, oxaprozin, leflunomide, diclofenac, nabumetone, acetyl coenzyme Q10, ibuprofen, flurbiprofen, tetrahydracannabinol, capsaicin, ketorolac, albendazole, ivermectin, amiodarone, zileuton, zafirlukast, albuterol, montelukast, azithromycin, ciprofloxacin, clarithromycin, dirithromycin, rifabutin, rifapentine, trovafloxacin, baclofen, ritonavir, saquinavir, nelfinavir, cfavirenz, dicumarol, tirofiban, cilostazol, ticlopidine, clopidogrel, oprelvekin, paroxetine, sertraline, venlafaxine, bupropion, clomipramine, miglitol, repaglinide, glimepiride, pioglitazone, rosiglitazone, troglitazone, glyburide, glipizide, glibenclamide, carbamazepine, fosphenytoin, tiagabine, topiramate, lamotrigine, vigabatrin, amphotericin B, butenafine, terbinafine, itraconazole, fluconazole, miconazole, lycopene, ketoconazole, metronidazole, griscofulvin, nitrofurantoin, spironolactone, lisinopril, benazepril, nifedipine, nisoldipine, telmisartan, irbesartan, cprosartan, valsartan, candesartan, minoxidil, terazosin, halofantrine, mefloquine, dihydroergotamine, ergotamine, frovatriptan, pizotifen, sumatriptan, zolmitriptan, naratriptan, rizatriptan, aminoglutethimide, busulfan, cyclosporin, mitoxantrone, irinotecan, etoposide, teniposide, paclitaxel, tacrolimus, sirolimos, tamoxifen, camptothecin, topotecan, nilutanide, bicalutanide, ephedrine, toremifene, atovaquone, furazolidone, paricalcitol, benzonatate, midazolam, zolpidem, gabapentin, zopiclone, digoxin, beclomethasone, budesonide, betamethasone, prednisolone, cisapride, cimetidine, loperamide, famotidine, lansaprazole, rabeprazole, nizatidine, omeprazole, cetirizine, cinnarizine, dexchlorphentramini, loratadine, clemastine, fexofenadine, chlorpheniramine, acetretin, tazarotene, calcipotriene, calcitriol, targretin, ergocalciferol, cholecalciferol, isotretinoin, tretinoin, calcifediol, fenofibrate, probucol, gemfibrozil, cerivastatin, pravastatin, simvastatin, fluvastatin, atorvastatin, tizanidine, dantrolene, isosorbide dinitrate, codeine, fentanyl, methadone, nalbuphine, pentazocine, clomiphene, danazol, dehydroepiandrosterone, medroxyprogesterone, progesterone, rimexolone, megestrol acetate, oestradiol, finasteride, mifepristone, amphetamine, L-thyroxine, tamsulosin, methoxsalen, tacrine, donezepil, raloxifene, verteporfrin, sibutramine, and pyridostigmine.

Salts, derivatives, isomers and mixtures of polyfunctional active ingredients can also be used.

The emulsions of the present invention can be produced by methods known in the art for forming emulsions, and examples of particular methods are shown in the Examples herein. It should be understood that formulation factors such as active characteristics, packaging, excipient purity and sourcing, and processing factors, such as sequence or method of excipient/drug addition, energy input, and sterilization cycle factors affect the commercial viability or therapeutic benefit of any given emulsion product.

An example of a typical process is as follows: An appropriate amount of the polyfunctional active is dissolved in the desired oil phase containing the appropriate polarity modifier(s) at the desired temperature. To further increase the load of the polyfuctional active or to facilitate the process, the active can be solubilized in an appropriate solvent or mixture of solvents prior to adding active to the oil phase. The solvents used in such processes can then be partially or completely removed, depending on the tolerance of the formulation to the residual solvents. Appropriate polarity modifier can also be added to the solvent along with the active. Alternatively, in the presence of the polarity modifier, the solvent can be removed prior to mixing with the other oil components. The emulsifier, such as a phospholipid, can be dispersed in the oil phase directly, or it can be dispersed in an aqueous solution of glycerol or other tonicfier, with or without an antioxidant and with or without a preservative at the desired temperature. Chelators or bufferants can also be optionally included to improve stability of the final product.

The oil solution is then mixed with an aqueous solution at an appropriate temperature and for a sufficient amount of time to fully emulsify the oil. The mean diameter of the resulting coarse emulsion is preferably less than 20 microns. The resulting mixture is further homogenized at a desired pressure in batch-wise or continuous cycles until the desired particle size is obtained, typically a submicron particle size. Several high pressure homogenizers are available for this process, including EmulsiFlex (Avestin), microfluidizer (Microfluidics), and Rannie homogenizer (APV). The resulting emulsion can be further pH adjusted and heat-, filter-, or radiation-sterilized.

Of course, in embodiments which do not include a polyfunctional active ingredient, the same general procedure can be followed, omitting the active.

Preferred emulsions can have a mean particle diameter of less than about 5 $\mu$m, preferably less than about 2 $\mu$m, more preferably less than about 1 $\mu$m, still more preferably less than about 0.5 μm, and most preferably less than about 0.3 μm. Particle size can be determined by conventional methods, such as by measurement with a particle size analyzer.

In another embodiment, the present invention is directed to a pharmaceutical emulsion for delivery of a polyfunctional active ingredient as described above, wherein the oil phase of the emulsion includes a long chain triglyceride, and at least one compound selected from the group consisting of acids, bases, monoglycerides, diglycerides, acetylated monoglycerides; acetylated diglycerides; bile acids; cholesterol; cholesterol fatty acid esters; fatty acids; fatty alcohols; fusidic acids; lactic acid derivatives of mono/diglycerides; lower alcohol fatty acid esters; propylene glycol fatty acid esters; polyol fatty acid esters; polyol alkyl ethers; lipophilic reaction mixtures of polyols and at least one member of the group consisting of fatty acids, glycerides, vegetable oils, hydrogenated vegetable oils, and sterols: sorbitan fatty acid esters; polyethoxylated esters; polyethoxylated alkyl ethers; and polyethoxylated sterols. In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the oil phase includes a long chain triglyceride and at least one compound selected from the group consisting of monoglycerides; diglycerides; acetylated monoglycerides; acetylated diglycerides; bile acids; cholesterol; cholesterol fatty acid esters; fatty acids; fatty alcohols; fusidic acids; lactic acid derivatives of mono/diglycerides; lower alcohol fatty acid esters; propylene glycol fatty acid esters; polyol fatty acid esters; polyol alkyl ethers; lipophilic reaction mixtures of polyols and at least one member of the group consisting of fatty acids, glycerides, vegetable oils, hydrogenated vegetable oils, and sterols; sorbitan fatty acid esters; polyethoxylated esters; polyethoxylated alkyl ethers; polyethoxylated sterols; and mixtures thereof. In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the oil phase includes a long chain triglyceride and at least one compound selected from the group consisting of acids; bases; acetylated monoglycerides; acetylated diglycerides; bile acids; cholesterol; cholesterol fatty acid esters; fatty acids; fatty alcohols; fusidic acids; lactic acid derivatives of mono/diglycerides; lower alcohol fatty acid esters; propylene glycol fatty acid esters; polyol fatty acid esters; polyol alkyl ethers; lipophilic reaction mixtures of polyols and at least one member of the group consisting of fatty acids, glycerides, vegetable oils, hydrogenated vegetable oils, and sterols; sorbitan fatty acid esters; polyethoxylated esters; polyethoxylated alkyl ethers; polyethoxylated sterols; and mixtures thereof. In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the oil phase includes a long chain triglyceride and at least one compound selected from the group consisting of acids; bases; monoglycerides; diglycerides; bile acids; cholesterol; cholesterol fatty acid esters; fatty acids; fatty alcohols; fusidic acids; lactic acid derivatives of mono/diglycerides; lower alcohol fatty acid esters; propylene glycol fatty acid esters; polyol fatty acid esters; polyol alkyl ethers; lipophilic reaction mixtures of polyols and at least one member of the group consisting of fatty acids, glycerides, vegetable oils, hydrogenated vegetable oils, and sterols; sorbitan fatty acid esters; polyethoxylated esters; polyethoxylated alkyl ethers; polyethoxylated sterols; and mixtures thereof. In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the oil phase includes a long chain triglyceride and at least one compound selected from the group consisting of monoglycerides; diglycerides; acetylated monoglycerides; acetylated diglycerides; cholesterol fatty acid esters; fatty alcohols; lower alcohol fatty acid esters; propylene glycol fatty acid esters; polyol fatty acid esters; lipophilic reaction mixtures of polyols and at least one member of the group consisting of fatty acids, glycerides, vegetable oils, hydrogenated vegetable oils, and sterols; sorbitan fatty acid esters; polyethoxylated esters; polyethoxylated alkyl ethers; polyethoxylated sterols; and mixtures thereof. In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the oil phase includes a long chain triglyceride and at least one compound selected from the group consisting of acids; bases; acetylated monoglycerides; acetylated diglycerides; cholesterol fatty acid esters; fatty alcohols; lactic acid derivatives of mono/diglycerides; lower alcohol fatty acid esters; propylene glycol fatty acid esters; polyol fatty acid esters; polyol alkyl ethers; lipophilic reaction mixtures of polyols and at least one member of the group consisting of fatty acids, glycerides, vegetable oils, hydrogenated vegetable oils, and sterols; sorbitan fatty acid esters; polyethoxylated esters; polyethoxylated alkyl ethers; polyethoxylated sterols; and mixtures thereof. In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the oil phase includes a long chain triglyceride and at least one compound selected from the group consisting of acids; bases; monoglycerides; diglycerides; cholesterol fatty acid esters; fatty alcohols; fusidic acids; derivatives of mono/diglycerides; lower alcohol fatty acid esters; propylene glycol fatty acid esters; polyol fatty acid esters; polyol alkyl ethers; lipophilic reaction mixtures of polyols and at least one member of the group consisting of fatty acids, glycerides, vegetable oils, hydrogenated vegetable oils, and sterols; sorbitan fatty acid esters; polyethoxylated esters; polyethoxylated alkyl ethers; polyethoxylated sterols; and mixtures thereof. In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the oil phase includes a long chain triglyceride and at least one compound selected from the group consisting of acetylated monoglycerides; acetylated diglycerides; bile acids; cholesterol; cholesterol fatty acid esters; fatty acids; fatty alcohols; fusidic acids; lactic acid derivatives of mono/diglycerides; lower alcohol fatty acid esters; propylene glycol fatty acid esters; polyol fatty acid esters; polyol alkyl ethers; lipophilic reaction mixtures of polyols and at least one member of the group consisting of fatty acids, glycerides, vegetable oils, hydrogenated vegetable oils, and sterols; sorbitan fatty acid esters; polyethoxylated esters; polyethoxylated alkyl ethers; polyethoxylated sterols; and mixtures thereof. In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the oil phase includes a long chain triglyceride and at least one compound selected from the group consisting of monoglycerides; diglycerides; bile acids; cholesterol; cholesterol fatty acid esters; fatty acids; fatty alcohols; fusidic acids; lactic acid derivatives of mono/diglycerides; lower alcohol fatty acid esters; propylene glycol fatty acid esters; polyol fatty acid esters; polyol alkyl ethers; lipophilic reaction mixtures of polyols and at least one member of the group consisting of fatty acids, glycerides, vegetable oils, hydrogenated vegetable oils, and sterols; sorbitan fatty acid esters; polyethoxylated esters; polyethoxylated alkyl ethers; polyethoxylated sterols; and mixtures thereof. In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the oil phase includes a long chain triglyceride and at least one compound selected from the group consisting of acids; bases; bile acids; cholesterol; cholesterol fatty acid esters; fatty acids; fatty alcohols; fusidic acids; lactic acid derivatives of mono/diglycerides; lower alcohol fatty acid esters; propylene glycol fatty acid esters; polyol fatty acid esters; polyol alkyl ethers; lipophilic reaction mixtures of polyols and at least one member of the group consisting of fatty acids, glycerides, vegetable oils, hydrogenated vegetable oils, and sterols; sorbitan fatty acid esters; polyethoxylated esters; polyethoxylated alkyl ethers; polyethoxylated sterols; and mixtures thereof In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the oil phase includes a long chain triglyceride and at least one compound selected from the group consisting of bile acids; cholesterol; cholesterol fatty acid esters; fatty acids; fatty alcohols; fusidic acids; lactic acid derivatives of mono/diglycerides; lower alcohol fatty acid esters; propylene glycol fatty acid esters; polyol fatty acid esters; polyol alkyl ethers; lipophilic reaction mixtures of polyols and at least one member of the group consisting of fatty acids, glycerides, vegetable oils, hydrogenated vegetable oils, and sterols; sorbitan fatty acid esters; polyethoxylated esters; polyethoxylated alkyl ethers; polyethoxylated sterols; and mixtures thereof. In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the oil phase includes a long chain triglyceride, and at least one compound selected from the group consisting of monoglycerides, diglycerides, mixtures of mono- and diglycerides, and mixtures of mono-, di- and triglycerides. In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the oil phase includes a long chain triglyceride, and at least one compound selected from the group consisting of acetylated monoglycerides, acetylated diglycerides, and mixtures thereof. In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the oil phase includes a long chain triglyceride and a lipophilic reaction mixture, or a purified/fractionated lipophilic reaction mixture, of a polyol and at least one member of the group consisting of fatty acids, glycerides, vegetable oils, hydrogenated vegetable oils, and sterols. In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the oil phase includes a long chain triglyceride and at least one compound selected from the group consisting of polyethoxylated esters, polyethoxylated alkyl ethers, polyethoxylated sterols, and mixtures thereof. In this embodiment, the long chain triglyceride, the other components of the oil phase, and the emulsifier can be any of those previously described. The composition can further include a structured triglyceride, a polyfunctional active ingredient, or any of the other additives described above.

In another embodiment, the present invention is directed to a pharmaceutical emulsion for delivery of a polyfunctional active ingredient as described above, wherein the oil phase of the emulsion includes a water-immiscible triglyceride, and at least one pharmaceutically acceptable acid or pharmaceutically acceptable base. The water-immiscible triglyceride can be a long chain triglyceride or a structured triglyceride, and these and other components of the oil phase and the emulsifier can be any of those previously described. The composition can further include a polarity modifier, a structured triglyceride, a long chain triglyceride, a polyfunctional active ingredient, or any of the other additives described above.

The present invention is also directed to dosage forms of any of the pharmaceutical emulsions described herein. The dosage form can be the pharmaceutical emulsion processed by lyophilization, encapsulation, extrusion, homogenization, sonication, melting, solubilizing, evaporation, mixing, coating, size reduction, spraying, sterilization, filtration, irradiation, or a combination thereof It should be appreciated that the ability of the pharmaceutical composition to be processed by particular processing methods may depend upon the proper choice and sequence of processing steps, as is known to those skilled in the art.

The dosage form can be formulated as an injectable, a drink, an eye drop or spray, a nasal drop or spray, a buccal drop or spray, a cervical drop or spray, an inhalant, a lotion, a gel, a liniment, a cream, a paste, a solution, a suppository, an ovule, a wafer, a troche, a sachet, an elixir, a tincture, a douche, an aerosol, a patch, or a combination thereof, and can be adapted for parenteral, enteral, ocular, nasal, sublingual, buccal, topical, intra-cervical, rectal, intramuscular, intra-dermal, pulmonary, transmucosal, intra-thecal, intravenous, intra-arterial, epidural, intra-cavity, intra-organ transdermal, intra-lymphatic, intra-cranular, or intra-tumoral administration, or a combination thereof. Preferred dosage forms are those adapted for parenteral and pulmonary administration.

Preferably, the dosage form also includes a polyfunctional active ingredient, although in some circumstances it may be desirable to formulate the polyfunctional active ingredient in a separate dosage form for administration to a patient prior to, concurrently with, or subsequently to, administration of the pharmaceutical emulsion. When the dosage form includes a polyfunctional active ingredient, the active ingredient can be present in a therapeutically effective amount, as determined by one skilled in the art according to the pharmacological effect of the active ingredient, the needs of the patient, and other considerations well known in the art. In addition, part of the therapeutically effective amount of the polyfunctional active ingredient can also be formulated as a separate dosage form.

In another aspect, the present invention is directed to methods of treating an animal with a polyfunctional active ingredient. The method includes the steps of administering to the animal a dosage form of a pharmaceutical emulsion, as described above, and a therapeutically effective amount of a polyfunctional active ingredient. The active ingredient can be present in the dosage form of the pharmaceutical emulsion, in a separate dosage form, or both. The polyfunctional active ingredient can be administered to the animal prior to, concurrently with, or subsequent to, administering the dosage form of the pharmaceutical emulsion. The animal is preferably a mammal, and more preferably a human. Suitable emulsions include any of the emulsions described above.

In another aspect, the present invention is directed to methods of treating a patient with a pharmaceutical composition, wherein the composition includes effective amounts of an oil phase and an emulsifier. The amounts and components of the oil phase and emulsifier are effective to minimize drug precipitation upon administration, irritation and local toxicity at the site of administration; to alter drug biodistribution and clearance; and to minimize systemic drug toxicity, multi-drug resistance, intra-subject performance variability and/or inter-subject performance variability.

In use, the compositions and methods of the present invention provide significant advantages over conventional formulations of polyfunctional active ingredients. These advantages include:

1. The present compositions are free of toxic hydrophilic polyethoxylated surfactants, such as Cremophors® and Tweens®, that are traditionally used in parenteral formulations of polyfunctional hydrophobic active ingredients. By substantially reducing the need for these toxic surfactants, the present compositions eliminate potentially serious side effects associated with polyethoxylated surfactants, including potential hemolytic activity. In addition, compositions free of Cremophor EL also have the advantage of being compatible with plasticized PVC infusion devices.

2. Potential reduction in irritation, thrombophlebitis, and necrosis of local tissue at the injection site. Without wishing to be bound by theory, it is believed that being void of the large amount of surfactants present in the currently commercially available formulations of polyfunctional active ingredients, the present emulsion formulations can alleviate irritation, thrombophlebitis, and necrosis of local tissue at the injection site. In addition, these emulsion formulations are believed to reduce the irritation and necrosis of local tissue at the injection site caused by the direct contact with the irritating/cytotoxic actives by encapsulating the actives inside the oil phase. For hydrophobic or hydrophilic actives that are intrinsically irritating, encapsulation in emulsion droplets enables the active to overcome this limitation.

3. Ease of administration. Current polyethoxylated surfactant-containing formulations require dilution in 0.9% sodium chloride injection or 5% dextrose injection to different extents immediately before intravenous infusion, depending on the concentration of the surfactant present in the formulations. However, for a hydrophilic surfactant-free emulsion formulation, no extra step is expected to dilute the formulation prior to administration, thus potentially reducing costs and eliminating the chance of mistakes inherent in the extra step of dilution.

4. Higher loading capacity for polyfunctional hydrophobic actives than long chain triglyceride-based emulsion formulations, and more stable than medium chain-based emulsions. Structured triglycerides are believed to have a higher solubilizing potential for polyfunctional hydrophobic actives than do long chain triglycerides alone. The presence of shorter chain fatty acid groups makes the structured triglyceride more polar than long chain triglycerides, but not so polar as to negatively affect drug solubility and product stability, as is believed to be the case with medium chain triglycerides. These stable, higher drug loading formulations offer more practical dosing and rates of infusions without undesirable excessive lipid and volume doping in patients. Moreover, higher drug loading present sufficient production, storage, and shipping opportunities.

5. Fewer side effects than MCT-based emulsion formulations. By avoiding the use of medium chain triglycerides, and minimizing the amounts of compounds which can hydrolyze to medium chain fatty acids, the adverse effects observed with parenteral MCT emulsion formulations reported in animal studies can be minimized. In addition, structured triglycerides are known to offer improved protein sparing, weight gain, N balance and hepatic and muscle protein synthesis. Structured triglycerides do not increase energy expenditure as do MCTs, nor do structured triglycerides adversely affect the RES. Presumably, these effects are due to the structured triglycerides having intermediate clearance and oxidation rates, relative to LCTs and MCTS. Since the hydrolysis of structured triglycerides is slower than that of MCTs, it is believed that the adverse hemodynamic effects associated with uncontrolled excess build up of medium chain fatty acid concentrations are eliminated.

6. Safer additives. Polarity modifiers, such as mono- and diglycerides, especially of longer chain fatty acids, are expected to be less "leaky" from the oil particles upon injection, or less prone to rapid debinding/desorption from the lipoprotein blood fraction, due to the high hydrophobicity. Thus, these additives have lower free monomer activity in the blood, leading to superior bioacceptability of additives relative to high HLB surfactants.

7. Compatibility with plasticized PVC-containing packaging material, infusion equipment and devices. Since medium chain triglycerides are stronger solvents for some plasticizers, such as phthalates, MCT-based emulsions must be stored in glass containers and administered through specialized infusion equipment and devices. MCT-free or reduced chain emulsions have the benefits of lowering the manufacturing cost and reducing the potential hazards to patients and to the environment.

8. Greater stability over current emulsion formulations. It has been demonstrated that bile salts, such as cholate and deoxycholate, can improve the stability of oil-in-water emulsions. Presumably, surface active bile salts can orient themselves at the oil-water interface in such a way as to fix the structural defects on the interfacial membrane primarily composed of phospholipids, or can interact with the phospholipids, thus preventing the dissociation of phospholipids from the interface.

The stability of the emulsion also can be improved by charge repulsion imparted by the incorporation of appropriate charged or charge-inducing emulsifiers or polarity modifiers to the emulsion formulation. Typically, a negatively charged phospholipid, such as DMPG, can decrease the zeta potential of the emulsion particles (or increase the surface charge) to about −30 to −60 mV, which would provide significant repulsion forces to prevent the emulsion particles from agglomeration, fusion, etc. Similarly, polyethoxylated surfactants, amphiphilic synthetic polymers and certain amphiphilic proteins/peptides, can form shields surrounding emulsion particles to prevent the close contact of two or more particles through steric hindrance. The enormous van der Waals forces will repel particles when the shields of different particles are approaching to a close distance.

In the case of emulsions which contain a polyfunctional active ingredient, the stability of the active can potentially be improved. For actives are prone to hydrolysis, the oil droplets would shield the actives from the outside aqueous environment. As a result, the polyfunctional active formulated in the present emulsions should enjoy better stability upon storage compared to those in a cosolvent system, for example. For those actives that are prone to enzymatic degradation in a biological milieu upon administration, the emulsion oil droplets can potentially protect the active from enzymatic attack by making the active less accessible to enzymes such as esterase, peptidase, nuclease, etc.

9. More favorable binding. The emulsions composition of the present invention, through the unique combination of the polarity modifiers as well as the emulsifiers, possess unique size, surface, and polarity characteristics to alter the biodistribution and clearance of the emulsion particles as well as the pharmacokinetic and pharmacological profile of the polyfunctional actives either incorporated in the emulsion formulation or co-administered with the emulsion. These altered characteristics of the actives and the emulsion oil droplets are potentially useful in targeting the actives to a variety of cells, tissue, and organs. Such compositions can be injected directly to a target organ or a tumor to improve the therapeutic performance of the active. This can potentially lead to the improvement of efficacies of current indications as well as to the discovery of new indications with existing actives. Since the polyfunctional active can be delivered more effectively to the site of action, the undesirable exposure of the active to other local tissues or systemic circulation could be reduced. This will lead to the reduction of systemic or local toxicity.

For example, the binding profile of hydrophobic polyfunctional actives to blood components such as erythrocytes, lymphocytes, platelet, and plasma proteins including albumin, α-acid glycoprotein, lipoproteins, etc., can be modulated by the interaction of the polarity modifiers as well as the emulsifiers with the blood components or the drugs themselves. Targeted, more favorable binding to the lipoprotein fraction results in an altered biodistribution and clearance. More selective binding to specific fractions, such as high density lipoprotein, can potentially reduce toxicity and reduce variability in patients with varying cholesterol levels.

Relatively more hydrophilic polyfunctional actives, including conventional anti-infectives, peptides, and oligonucleotides, can be sequestered into the emulsion oil phase as a result of the interactions with the polarity modifiers. Consequently, the circulating half-time of typical low-molecular weight water-soluble compounds can frequently be prolonged significantly. This will enable these actives to circulate and accumulate to an effective level at the site of action, such as brain, liver, and sites of inflammation or solid tumors. It is also possible that this will alleviate the toxicity of the active toward organs, such as the kidney and liver, involved in the clearance of the active.

In addition, the emulsion formulations of the present invention can further include a ligand or receptor on the surface of the emulsion particles to promote more specific recognition between the emulsion particles and the intended sites for targeted delivery. For example, an antibody can be grafted to the surface of the emulsion particles to specifically target cancerous cells expressing particular antigens recognized by the antibody. Through such antibody-antigen interaction, a given anticancer drug can be more effectively delivered to the site of action by the emulsion formulation to alleviate potential dose-limiting systemic toxicity.

10. Parenteral formulations. The present compositions provide another needed administration option, the parenteral route, to the current therapeutic choices. For example, azole antifungal agents with systemic efficacy currently do not have a parenteral product available. Such polyfunctional actives can be effectively formulated in parenteral dosage forms of the pharmaceutical emulsions of the present invention for therapeutic benefit or bioavailability assessment in product development.

11. Better calorie control, such as in applications when faster energy production is needed in critically ill patients. The present compositions offer faster energy production than plain long chain triglycerides, but slower than medium chain triglycerides, which could be unsafe in some situations.

12. Taste masking. For delivery of unpalatable active ingredients, emulsions provide benefits by incorporating the active ingredient into the oil phase, thus lowering its activity in the aqueous phase coming into contact with the palate.

13. Benefits in delivery, storage and dosing. Unlike solid particulate delivery for pulmonary, nasal or buccal delivery, the present compositions offer more reproducible, bioacceptable emulsion particles of size more amenable to better absorption from the absorption site, consistent dosing, and better storage properties.

EXAMPLES

Example 1

Cyclosporin Emulsion I

An emulsion according to the present invention was prepared, with cyclosporin A as the polyfunctional active ingredient dissolved in an oil phase including a structured triglyceride (Captex 810D) and a long chain triglyceride (safflower oil). The emulsion had the following components:

| Component | % (w/w) |
| --- | --- |
| Cyclosporin A | 1.0 |
| Captex 810D | 5.0 |
| Safflower Oil USP | 5.0 |
| BHT | 0.02 |
| Egg Phospholipid | 2.4 |
| DMPG* | 0.2 |
| Glycerol | 2.25 |
| EDTA | 0.01 |
| Water | q.s. |

*dimyristoyl phosphatidyl glycerol

The emulsion was prepared as follows. Captex 810D and safflower oil were mixed to form a homogeneous oil. Cyclosporin A and BHT were added to the oil and dissolved at room temperature. Egg phospholipid and DMPG were added to the oil mixture and dispersed in the oil phase. The oil phase was heated to 60°–70° C., then added to an aqueous phase of water, glycerol and EDTA. The mixture was then mixed well using an UltraTurrax homogenizer (IKA). The mixture was further high pressure homogenized by a microfluidizer (Microfluidics) at a pressure of 16,000 psi for 10 cycles in succession. The resulting emulsion had a mean particle diameter of less than 300 nm, as measured by a Nicomp particle size analyzer (Particle Size Systems, Inc.).

Example 2
Cyclosporin Emulsion II

An emulsion according to the present invention was prepared, with cyclosporin A as the polyfunctional active ingredient dissolved in an oil phase including a structured triglyceride (Captex 810D) and polarity modifiers (monoglycerides and acetylated monoglycerides). The emulsion had the following components:

| Component | % (w/w) |
| --- | --- |
| Cyclosporin A | 1.0 |
| Captex 810D | 7.0 |
| Eastman 9-45* | 2.0 |
| Peceol** | 1.0 |
| Egg Phospholipid | 3.6 |
| Glycerol | 2.25 |
| EDTA | 0.01 |
| Water | q.s. |

*acetylated monoglycerides
**monoglycerides

The emulsion was prepared as follows. Captex 810D, Eastman 9-45 and Peceol were mixed to form a homogeneous oil. Cyclosporin A was added to the oil and dissolved at room temperature. Egg phospholipid was added to the oil mixture and dispersed in the oil phase. The oil phase was heated to 60°–70° C., then added to an aqueous phase of water, glycerol and EDTA. The mixture was then mixed well using an UltraTurrax homogenizer (IKA). The mixture was further high pressure homogenized by a microfluidizer (Microfluidics) at a pressure of 16,000 psi for 10 cycles in succession. The resulting emulsion had a mean particle diameter of less than 200 nm, as measured by a Nicomp particle size analyzer (Particle Size Systems, Inc.).

Example 3
Cyclosporin Emulsion III

An emulsion according to the present invention was prepared, with cyclosporin A as the polyfunctional active ingredient dissolved in an oil phase including a long chain triglyceride (safflower oil) and a polarity modifier (acetylated monoglycerides). The emulsion had the following components:

| Component | % (w/w) |
| --- | --- |
| Cyclosporin A | 1.0 |
| Safflower Oil USP | 8.0 |
| Eastman 9-45* | 2.0 |
| BHT | 0.02 |
| Egg Phospholipid | 2.4 |
| Glycerol | 2.25 |
| EDTA | 0.01 |
| Water | q.s. |

*acetylated monoglycerides

The emulsion was prepared as follows. Safflower oil and Eastman 9-45 were mixed to form a homogeneous oil. Cyclosporin A and BHT were added to the oil and dissolved at room temperature. Egg phospholipid was dispersed in an aqueous phase containing water, glycerol and EDTA. Both the oil phase and the aqueous phase were heated to 60°–70° C., then combined and mixed well using an UltraTurrax homogenizer (IKA). The mixture was further high pressure homogenized by a microfluidizer (Microfluidics) at a pressure of 16,000 psi for 10 cycles in succession. The resulting emulsion had a mean particle diameter of less than 300 nm, as measured by a Nicomp particle size analyzer (Particle Size Systems, Inc.).

Example 4
Progesterone Emulsion I

An emulsion according to the present invention was prepared, with progesterone as the polyfunctional active ingredient dissolved in an oil phase including a long chain triglyceride (soybean oil) and polarity modifiers (monoglycerides and acetylated monoglycerides). The emulsion had the following components:

| Component | % (w/w) |
| --- | --- |
| Progesterone | 0.3 |
| Soybean Oil USP | 6.0 |
| Eastman 9-45* | 3.0 |
| Peceol** | 1.0 |
| BHT | 0.02 |
| Egg Phospholipid | 2.4 |
| Glycerol | 2.25 |
| EDTA | 0.01 |
| Water | q.s. |

*acetylated monoglycerides
**monoglycerides

The emulsion was prepared as follows. Soybean oil, Eastman 9-45 and Peceol were mixed to form a homogeneous oil. Progesterone and BHT were added to the oil and dissolved at room temperature. Egg phospholipid was added to the oil mixture and dispersed in the oil phase. The oil mixture was heated to 60° C.–70° C., then added to an aqueous phase containing water, glycerol and EDTA. The mixture was mixed well using an UltraTurrax homogenizer (IKA). The mixture was further high pressure homogenized by a microfluidizer (Microfluidics) at a pressure of 16,000 psi for 10 cycles in succession. The resulting emulsion had a mean particle diameter of less than 200 nm, as measured by a Nicomp particle size analyzer (Particle Size Systems, Inc.).

Example 5
Progesterone Emulsion II

An emulsion according to the present invention was prepared, with progesterone as the polyfunctional active ingredient dissolved in an oil phase including a structured triglyceride (Captex 810D), a long chain triglyceride (glycerol trioleate), and a polarity modifier (mono-, diglyceride mixture). The emulsion had the following components:

| Component | % (w/w) |
|---|---|
| Progesterone | 0.3 |
| Captex 810D | 4.0 |
| Captex GTO* | 4.0 |
| Capmul MCM** | 2.0 |
| BHT | 0.02 |
| Egg Phospholipid | 2.4 |
| DMPG*** | 0.4 |
| Glycerol | 2.25 |
| EDTA | 0.01 |
| Water | q.s. |

*glycerol trioleate
**mixture of monoglycerides and diglycerides
***dimyristoyl phosphatidyl glycerol The emulsion was prepared as follows. Captex 810D, Captex GTO and Capmul MCM were mixed to form a homogeneous oil. Progesterone and BHT were added to the oil and dissolved at room temperature. Egg phospholipid and DMPG were dispersed in an aqueous phase containing water, glycerol and EDTA. Both the oil phase and the aqueous phase were heated to 60° C.–70° C., then combined and mixed well using an UltraTurrax homogenizer (IKA). The mixture was further high pressure homogenized by a microfluidizer (Microfluidics) at a pressure of 16,000 psi for 10 cycles in succession. The resulting emulsion had a mean particle diameter of less than 150 nm, as measured by a Nicomp particle size analyzer (Particle Size Systems, Inc.).

Example 6
Tretinoin Emulsion I

An emulsion according to the present invention was prepared, with tretinoin as the polyfunctional active ingredient dissolved in an oil phase including a long chain triglyceride (safflower oil), an oil-miscible base (triethylamine) and polarity modifiers (acetylated monoglycerides and a mono-,diglyceride mixture). The emulsion had the following components:

| Component | % (w/w) |
|---|---|
| Tretinoin | 0.2 |
| Triethylamine | 0.1 |
| Safflower Oil USP | 6.0 |
| Eastman 9-45* | 2.0 |
| Imwitor 988** | 2.0 |
| BHT | 0.02 |
| Egg Phospholipid | 1.2 |
| Glycerol | 2.25 |
| EDTA | 0.01 |
| Water | q.s. |

*acetylated monoglycerides
**mixture of monoglycerides and diglycerides

The emulsion was prepared as follows Safflower oil, triethylamine, Eastman 9-45 and Imwitor 988 were mixed to form a homogeneous oil Tretinoin and BHT were added to the oil and dissolved at room temperature. Egg phospholipid was dispersed in an aqueous phase containing water, glycerol and EDTA. Both the oil phase and the aqueous phase were heated to 60° C.–70° C., then combined and mixed well using an UltraTurrax homogenizer (IKA). The mixture was further high pressure homogenized by a microfluidizer (Microfluidics) at a pressure of 16,000 psi for 10 cycles in succession. The resulting emulsion had a mean particle diameter of less than 100 nm, as measured by a Nicomp particle size analyzer (Particle Size Systems, Inc.).

The Example was repeated, but after combining the oil and aqueous phases, the mixture was sonicated at room temperature using a Branson sonifier. The pooled sonified material was then high pressure homogenized as previously described. The resulting emulsion had mean particle diameter of less than 80 nm.

Example 7
Tretinoin Emulsion II

An emulsion according to the present invention was prepared, with tretinoin as the polyfunctional active ingredient dissolved in an oil phase including a structured triglyceride (Captex 810 D), an oil-miscible base (triethylamine) and polarity modifiers (monoglycerides and a mono-,diglyceride mixture). The emulsion had the following components:

| Component | % (w/w) |
|---|---|
| Tretinoin | 0.2 |
| Triethylamine | 0.1 |
| Captex 810D | 6.0 |
| Peceol* | 3.0 |
| Capmul MCM** | 1.0 |
| BHT | 0.02 |
| Egg Phospholipid | 1.2 |
| Glycerol | 2.25 |
| EDTA | 0.01 |
| Water | q.s. |

*monoglycerides
**mixture of monoglycerides and diglycerides

The emulsion was prepared as follows. Captex 810D, triethylamine, Peceol and Capmul MCM were mixed to form a homogeneous oil. Tretinoin and BHT were added to the oil and dissolved at room temperature. Egg phospholipid was dispersed in an aqueous phase containing water, glycerol and EDTA. Both the oil phase and the aqueous phase were heated to 60° C.–70° C., then combined and mixed well using an UltraTurrax homogenizer (IKA). The mixture was further high pressure homogenized by a microfluidizer (Microfluidics) at a pressure of 16,000 psi for 10 cycles in succession. The resulting emulsion had a mean particle diameter of less than 100 nm, as measured by a Nicomp particle size analyzer (Particle Size Systems, Inc.).

Example 8
Ketoconazole Emulsion

An emulsion according to the present invention can be prepared, with ketoconazole as the polyfunctional active ingredient dissolved in an oil phase including a long chain triglyceride (soybean oil), an oil-miscible acid (oleic acid) and a polarity modifier (acetylated monoglycerides). A suitable emulsion can have the following components:

| Component | % (w/w) |
| --- | --- |
| Ketoconazole | 1.0 |
| Oleic Acid | 2.0 |
| Soybean Oil USP | 6.0 |
| Eastman 9-45* | 4.0 |
| BHT | 0.02 |
| Egg Phospholipid | 2.4 |
| Glycerol | 2.25 |
| EDTA | 0.01 |
| Water | q.s. |

*acetylated monoglycerides

The emulsion can be prepared as follows. Soybean oil, oleic acid and Eastman 9-45 are mixed to form a homogeneous oil. Ketoconazole and BHT are added to the oil and dissolved at room temperature. Egg phospholipid is dispersed in an aqueous phase containing water, glycerol and EDTA. Both the oil phase and the aqueous phase are heated to 60° C.–70° C., then combined and mixed well using an UltraTurrax homogenizer (IKA). The mixture is further high pressure homogenized by a microfluidizer (Microfluidics) at a pressure of 16,000 psi for 10 cycles in succession.

Examples 9–14 illustrate pharmaceutical emulsions according to the present invention which do not contain an active ingredient. These emulsions are suitable for delivery of a wide variety of polyfunctional active ingredients, as described herein.

Example 9
Drug-Free Emulsion I

An emulsion according to the present invention was prepared with an oil phase including a structured triglyceride (Captex 810D), a long chain triglyceride (soybean oil), and a polarity modifier (low HLB polyethoxylated vegetable oil). The emulsion had the following components:

| Component | % (w/w) |
| --- | --- |
| Captex 810D | 6.0 |
| Soybean Oil USP | 4.0 |
| Labrafil M2125 CS* | 1.0 |
| Egg Phospholipid | 1.8 |
| Glycerol | 2.25 |
| EDTA | 0.01 |
| Water | q.s. |

*low HLB polyethoxylated vegetable oil

The emulsion was prepared as follows. Captex 810D, soybean oil and Labrafil M2125 CS were mixed to form a homogeneous oil. Egg phospholipid was dispersed in an aqueous phase containing water, glycerol and EDTA. Both the oil phase and the aqueous phase were heated to 60° C.–70° C., then combined and mixed well using an UltraTurrax homogenizer (IKA). The mixture was further high pressure homogenized by a microfluidizer (Microfluidics) at a pressure of 16,000 psi for 10 cycles in succession. The resulting emulsion had a mean particle diameter of less than 150 nm, as measured by a Nicomp particle size analyzer (Particle Size Systems, Inc.).

Example 10
Drug-Free Emulsion II

An emulsion according to the present invention was prepared with an oil phase including a structured triglyceride (Captex 810D), a long chain triglyceride (safflower oil), and a polarity modifier (propylene glycol fatty acid esters). The emulsion had the following components:

| Component | % (w/w) |
| --- | --- |
| Captex 810D | 6.0 |
| Safflower Oil USP | 4.0 |
| Lauroglycol FCC* | 1.0 |
| Egg Phospholipid | 1.8 |
| Glycerol | 2.25 |
| EDTA | 0.01 |
| Water | q.s. |

*propylene glycol fatty acid esters

The emulsion was prepared as follows. Captex 810D, safflower oil and Lauroglycol FCC were mixed to form a homogeneous oil. Egg phospholipid was dispersed in an aqueous phase containing water, glycerol and EDTA. Both the oil phase and the aqueous phase were heated to 60° C.–70° C., then combined and mixed well using an UltraTurrax homogenizer (IKA). The mixture was further high pressure homogenized by a microfluidizer (Microfluidics) at a pressure of 16,000 psi for 10 cycles in succession. The resulting emulsion had a mean particle diameter of less than 100 nm, as measured by a Nicomp particle size analyzer (Particle Size Systems, Inc.).

Example 11
Drug-Free Emulsion III

An emulsion according to the present invention was prepared with an oil phase including a long chain triglyceride (safflower oil), and a polarity modifier (polyglycerized fatty acid esters). The emulsion had the following components:

| Component | % (w/w) |
| --- | --- |
| Safflower Oil USP | 8.0 |
| Plurol Oleique CC497* | 2.0 |
| Egg Phospholipid | 1.2 |
| DPMG** | 0.2 |
| Glycerol | 2.25 |
| EDTA | 0.01 |
| Water | q.s. |

*polyglycerized fatty acid esters
**dimyristoyl phosphatidyl glycerol

The emulsion was prepared as follows. Safflower oil and Plurol Oleique CC497 were mixed to form a homogeneous oil. Egg phospholipid and DMPG were dispersed in an aqueous phase containing water, glycerol and EDTA. Both the oil phase and the aqueous phase were heated to 60° C.–70° C., then combined and mixed well using an UltraTurrax homogenizer (IKA). The mixture was further high pressure homogenized by a microfluidizer (Microfluidics) at a pressure of 16,000 psi for 10 cycles in succession. The resulting emulsion had a mean particle diameter of less than 100 nm, as measured by a Nicomp particle size analyzer (Particle Size Systems, Inc.).

Example 12
Drug-Free Emulsion IV

An emulsion according to the present invention was prepared with an oil phase including a long chain triglyceride (soybean oil) and a polarity modifier (low HLB polyethoxylated fatty acid esters). The emulsion had the following components:

| Component | % (w/w) |
|---|---|
| Soybean Oil USP | 9.0 |
| Kessco PEG 400 DO* | 1.0 |
| Egg Phospholipid | 1.8 |
| Glycerol | 2.25 |
| EDTA | 0.01 |
| Water | q.s. |

*low HLB polyethoxylated fatty acid esters

The emulsion was prepared as follows. Soybean oil and Kessco PEG 400DO were mixed to form a homogeneous oil. Egg phospholipid was dispersed in an aqueous phase containing water, glycerol and EDTA. Both the oil phase and the aqueous phase were heated to 60° C.–70° C., then combined and mixed well using an UltraTurrax homogenizer (IKA). The mixture was further high pressure homogenized by a microfluidizer (Microfluidics) at a pressure of 16,000 psi for 10 cycles in succession. The resulting emulsion had a mean particle diameter of less than 100 nm, as measured by a Nicomp particle size analyzer (Particle Size Systems, Inc.).

Example 13
Drug-Free Emulsion V

An emulsion according to the present invention was prepared with an oil phase including a structured triglyceride (Captex 810D) and a polarity modifier (mixture of mono-, di- and triglycerides). The emulsion had the following components:

| Component | % (w/w) |
|---|---|
| Captex 810D | 8.0 |
| Maisine 35-1* | 2.0 |
| Egg Phospholipid | 1.2 |
| DMPG** | 0.2 |
| Glycerol | 2.25 |
| EDTA | 0.01 |
| Water | q.s. |

*mixture of mono-, di- and triglycerides
**dimethyl propylene glycol

The emulsion was be prepared as follows. Captex 810D and Maisine 35-1 were mixed to form a homogeneous oil. Egg phospholipid and DMPG were dispersed in an aqueous phase containing water, glycerol and EDTA. Both the oil phase and the aqueous phase were heated to 60° C.–70° C., then combined and mixed well using an UltraTurrax homogenizer (IKA). The mixture was further high pressure homogenized by a microfluidizer (Microfluidics) at a pressure of 16,000 psi for 10 cycles in succession.

Example 14
Drug-Free Emulsion VI

An emulsion according to the present invention can be prepared with an oil phase including a structured triglyceride (Captex 810D), a long chain triglyceride (safflower oil) and an oil-dispersible acid (deoxycholic acid). The emulsion can have the following components:

| Component | % (w/w) |
|---|---|
| Captex 810D | 5.0 |
| Safflower Oil USP | 4.5 |
| Deoxycholic Acid | 0.5 |
| Egg Phospholipid | 2.4 |
| Glycerol | 2.25 |
| EDTA | 0.01 |
| Water | q.s. |

The emulsion can be prepared as follows. Captex 810D, safflower oil and deoxycholic acid are mixed to form a homogeneous oil. Egg phospholipid is dispersed in an aqueous phase containing water, glycerol and EDTA. Both the oil phase and the aqueous phase are heated to 60° C.–70° C., then combined and mixed well using an UltraTurrax homogenizer (IKA). The mixture is further high pressure homogenized by a microfluidizer (Microfluidics) at a pressure of 16,000 psi for 10 cycles in succession.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A stabilized pharmaceutical oil-in-water emulsion for delivery of a polyfunctional drug, wherein the emulsion has a mean particle diameter of less than about 5 μm and consists essentially of:
    (a) a therapeutically effective amount of a polyfunctional drug selected from the group consisting of analgesics, anti-inflammatory agents, anthelmintics, antiarrhythimic agents, anti-asthma agents, anti-bacterial agents, anti-viral agents, anti-coagulants, anti-depressants, anti-diabetic agents, anti-epileptic agents, anti-fungal agents, anti-gout agents, anti-hypertensive agents, antimalarials, anti-migraine agents, anti-muscarinic agents, anti-neoplostic agents, immunosuppressants, anti-protozoal agents, anti-thyroid agents, anti-tussives, anxiolytics, sedatives, hypnotics, neuroleptic agents, β-blockers, cardiac inotropic agents, corticosteroids, diuretics, anti-parkinsonism agents, gastrointestinal agents, histamine receptor antagonists, keratolytics, lipid regulating agents, muscle relaxants, anti-anginal agents, sex hormones, stimulants, cytokines, peptidomimetics, proteins, peptides, toxoids, antibodies, vaccines, nucleosides, nucleotides, nucleic acids, DNA, RNA, oligonucleotides, oligodeoxynucleotides, and combinations thereof;
    (b) an aqueous phase;
    (c) an oil phase consisting essentially of
        (i) a mixture of structured triglycerides having one medium chain fatty acid (MCFA) group and at least one long chain fatty acid (LCFA) groups, wherein the total amount of fatty groups of the oil phase having a carbon chain length of from 6–12 carbons atoms is less than about 30% and the total amount of fatty acid groups of the oil phase having a carbon chain length of greater than 12 carbon atoms is greater than 10% by weight, based on the total weight of the fatty acid groups of the oil phase, and
        (ii) a polarity modifier effective to facilitate the incorporation of the polyfunctional drug into the emulsion, wherein the polarity modifier is selected from the group consisting of inorganic acids and inorganic; and (d) an amount of an emulsifier effective to provide a stabilized emulsion suitable for parenteral administration, wherein the emulsifier is selected from the group consisting of ceramides, mixed chain phospholipids, cationic lipids, oligolipids, phospholipids, carnitines, sphingosines, sphingomyelins, glycolipids, lipoproteins, apoproteins, amphiphilic proteins, amphiphilic peptides, amphiphilic synthetic polymers, and combinations thereof.

2. The pharmaceutical emulsion of claim 1, wherein the polyfunctional drug is hydrophobic and has an intrinsic aqueous solubility of less than about 1 mg/mL.

3. The pharmaceutical emulsion of claim 2, wherein the polyfunctional drug has an intrinsic aqueous solubility of less than about 0.1 mg/mL.

4. The pharmaceutical emulsion of claim 1, wherein the polyfunctional drug is hydrophilic and has an octanol/water partition coefficient of less than about 100.

5. The pharmaceutical emulsion of claim 4, wherein the polyfunctional drug has an octanol/water partition coefficient of less than about 10.

6. The pharmaceutical emulsion of claim 1, wherein the oil phase is substantially free of triglycerides having three fatty acid groups with a carbon chain length of from 6 to 12 carbon atoms.

7. The pharmaceutical emulsion of claim 1, wherein the oil phase further comprises a vegetable oil, a fish oil, an animal fat, a hydrogenated vegetable oil, a partially hydrogenated vegetable oil, a semi-synthetic triglyceride, a synthetic triglyceride, or a mixture thereof.

8. The pharmaceutical emulsion of claim 1, wherein the oil phase further comprises almond oil; babassu oil; borage oil; black currant seed oil; canola oil; castor oil; coconut oil; corn oil; cottonseed oil; emu oil; evening primrose oil; flax seed oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; a mixture of hydrogenated cottonseed oil and hydrogenated castor oil; partially hydrogenated soybean oil; a mixture of partially hydrogenated soybean oil and partially hydrogenated cottonseed oil; glyceryl trioleate; glyceryl trilinoleate; glyceryl trilinolenate; a $\Omega 3$ polyunsaturated fatty acid triglyceride containing oil; or a mixture thereof.

9. The pharmaceutical composition of claim 1, wherein the oil phase further comprises coconut oil; corn oil; olive oil; palm oil; peanut oil; safflower oil; sesame oil; soybean oil; hydrogenated castor oil; hydrogenated coconut oil; partially hydrogenated soybean oil; glyceryl trioleate; glyceryl trilinoleate; glyceryl trilinolenate; a $\Omega 3$ polyunsaturated fatty acid triglyceride containing oil; or a mixture thereof.

10. The pharmaceutical composition of claim 1, wherein the oil phase further comprises corn oil; olive oil; palm oil; peanut oil; safflower oil; sesame oil; soybean oil; hydrogenated castor oil; partially hydrogenated soybean oil; glyceryl trioleate; glyceryl trilinoleate; a $\Omega 3$ polyunsaturated fatty acid triglyceride containing oil; or a mixture thereof.

11. The pharmaceutical emulsion of claim 1, wherein the total amount of LCFA groups in the oil phase is greater than about 30% by weight, based on the total weight of the fatty acid groups of the oil phase.

12. The pharmaceutical emulsion of claim 11, wherein the total amount of LCFA groups in the oil phase is greater than about 50% by weight, based on the total weight of the fatty acid groups of the oil phase.

13. The pharmaceutical emulsion of claim 1, wherein the emulsifier comprises a phospholipid selected from the group consisting of egg phospholipids, soy phospholipids, phosphatidylcholines, phosphatidylethanolamines, phosphatidylserines, phosphatidylglycerols, phosphatidylinositols, phosphatidic acids, mixed chain phospholipids, lysophospholipids, hydrogenated phospholipids, partially hydrogenated phospholipids, and mixtures thereof.

14. The pharmaceutical emulsion of claim 1, which further comprises glycerol, ethanol, propylene glycol, an antioxidant, an antiseptic, a buffering agent, a chelating agent, a colorant, a flavorant, an odorant, an osmotic modifier, a preservative, a solubilizer, a solvent, a tonicifier, a trace element, a viscomodulator, or a mixture thereof.

15. The pharmaceutical emulsion of claim 1, wherein the polyfunctional drug is selected from the group consisting of acarbose; acyclovir; acetyl cysteine; acetylcholine chloride; alatrofloxacin; alendronate; alglucerase; amantadine hydrochloride; ambenomium; amifostine; amiloride hydrochloride; aminocaproic acid; amphotericin B; antihemophilic factor (human); antihemophilic factor (poreine); antihemophilic factor (recombinant); aprotinin; asparaginase; atenolol; atracurium besylate; atropine; azithromycin; aztreonam; BCG vaccine; bacitracin; becaplemin; belladona; bepridil hydrochloride; bleomycin sulfate; calcitonin human; calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotaxime; cefoxitin sodium; ceftizoxime; ceftriaxone; cefuroxime axetil; cephalexin; cephapirin sodium; cholera vaccine; chorionic gonadotropin; cidofovir; cisplatin; cladribine; clidinium bromide; clindamycin and ciprofloxacin; clodronate; colistimethate sodium; colistin sulfate; corticotropin; cosyntropin; cromolyn sodium; cytarabine; dalteperin sodium; danaparoid; deferoxamine; denileukin diftitox; desmopressin; diatrizoate meglumine and diatrizoate sodium; dicyclomine; didanosine; dirithromycin; dopamine hydrochloride; dornase alpha; doxacurium chloride; doxorubicin; etidronate disodium; enalaprilat; enkephalin; enoxacin; enoxaparin sodium; ephedrine; epinephrine; epoetin alpha; erythromycin; esmolol hydrochloride; factor IX; famciclovir; fludarabine; fluoxetine; foscarnet sodium; ganciclovir; granulocyte colony stimulating factor; granulocyte-macrophage stimulating factor; recombinant human growth hormones; bovine growth hormones; gentamycin; glucagon; glycopyrolate; gonadotropin releasing hormone and synthetic analogs thereof, gonadorelin; grepafloxacin; haemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human; insulin lispro; insulin porcine; insulin NPH; insulin aspart; insulin glargine; insulin detemir; interferon alpha; interferon beta; ipratropium bromide; isophosphamide; Japanese encephalitis virus vaccine; lamivudine; leucovorin calcium; leuprolide acetate; levofloxacin; lincomycin and lincomycin derivatives; lobucavir; lomefloxacin; loracarbef, mannitol; measles virus vaccine; meningococcal vaccine; menotropins; mepenzolate bromide; mesalamine; methenamine; methotrexate; methscopolamine; metformin hydrochloride; metoprolol; mezlocillin sodium; mivacurium chloride; mumps viral vaccine; nedocromil sodium; neostigmine bromide; neostigmine methyl sulfate; neurontin; norfloxacin; oetreotide acetate; ofloxacin; olpadronate; oxytocin; pamidronate disodium; pancuronium bromide; paroxetine; pefloxacin; pentamidine isethionate; pentostatin; pentoxifylline; penciclovir, pentagastrin; phentolamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymyxin B sulfate; pralidoxime chloride; pramlintide; pregabalin; propaferone; propantheline bromide; pyridostigmine bromide; rabies vaccine; risedronate; ribavirin; rimantadine hydrochloride; rotavirus vaccine; salmeterol xinafoate; sincalide; small pox vaccine; sotalol; somatostatin; sparfloxacin; spectinomycin; stavudine; streptokinase; streptozocin; suxamethonium chloride; tacrine hydrochloride; terbutaline sulfate; thiotepa; ticarcillin; tiludronate; timolol; tissue type plasminogen activator; TNFR:Fc; TNK-tPA; trandolapril; trimetrexate gluconate; trospectomycin; trovafloxacin; tubocurarine chloride; tumor necrosis factor; typhoid vaccine live; urea; urokinase; vancomycin; valacyclovir; valsarian; varicella virus vaccine live; vasopressin and vasopressin; vecuronium bromide; vinblastine; vincristine; vinorelbine; warfarin sodium; yellow fever vaccine; zalcitabine; zanamivir; zoledronate; zidovudine; pharmacoutically acceptable salts, isomers, and derivative thereof; and mixtures thereof.

16. The pharmaceutical emulsion of claim 1, wherein the polyfunctional drug is selected from the group consisting of tramadol, celceoxib, etodolac, rofecoxib, oxaprozin, leflunomide, diclofenac, nabumetone, acetyl coenzyme Q10, ibuprofen, flurbiprofen, tetrahydrocannabinol, capsaicin, ketorolac, albendazole, ivermectin, amiodarone, zileuton, zafirlukast, albuterol, montelukast, azithromycin, ciprofloxacin, clarithromycin, dirithromycin, rifabutin, rifapentine, trovafloxacin, baclofen, ritonavir, saquinavir, nelfinavir, efavirenz, dicumarol, tirofiban, cilostazol, ticlopidine, clopidogrel, oprelyekin, paroxetine, sertraline, venlafaxine, bupropion, clomipramine, miglitol, repaglinide, glimepiride, pioglitazone, rosiglitazone, troglitazone, glyburide, glipizide, glibenclamide, carbamazenine, fosphenytoin, tiagabine, topiramate, lamotrigine, vigabatrin, amphotericin B, butenaline, terbinafine, itraconazole, fluconazole, miconazole, lycopene, ketoconazole, metronidazole, griseofulvin, nitrofurantoin, spironolactone, lisinopril, benazepril, nifedipine, nisoldipine, telmisartan, irbesartan, eprosartan, valsartan, candesartan, minoxidil, terazosin, halofantrine, mefloquine, dihydroergotamine, ergotamine, frovatriptan, pizotifen, sumatriptan, zolmitriptan, naratriptan, rizatriptan, aminoglutethimide, busulfan, cyclosporin, mitoxantrone, irinotecan, etoposide, teniposido, paclitaxel, tacrolimus, sirolimus, tamoxifen, camptothecin, topotecan, nilutanide, bicalutanide, ephedrine, toremifene, atovaquone, furazolidone, paricalcitol, benzonatate, midazolam, zolpidem, gabapentin, zopiclone, digoxin, beclomothasone, budesonide, betamethasone, prednisolone, cisapride, cimetidine, loperamide, famotidine, lansoprazole, rabeprazole, nizatidine, omeprazole, cetirizine, cinnarizine, dexchlorphenirarmine, loratadine, clemastine, fexofenadine, chlorpheniramine, acetretin, tazarotene, calcipotrieno, calcitriol, targretin, ergocalciferol, cholecalciferol, isotretinoin, tretinoin, calcifediol, fenofibrate, probucol, gemfibrozil, cerivastatin, pravastatin, simvastatin, fluvastatin, atorvastatin, tizanidine, dantrolene, isosorbide dinitrate, codeine, fentanyl, methadone, nalbuphine, pentazocine, clomiphene, danazol, dehydroepiandrosterone, medroxyprogesterone, progesterone, rimexolone, megostrol acetate, oestradiol, finasteride, mifepristone, amphetamine, L-thyroxine, tamsulosin, methoxsalen, facrine, donezepil, raloxifene, verteporfrin, sibutramine, pyridostigmine, pharmaceutically acceptable salts, isomers, and derivatives thereof; and mixtures thereof.

17. A dosage form of the pharmaceutical emulsion of claim 1.

18. The dosage form of claim 17, wherein the dosage form comprises the pharmaceutical emulsion processed by lyophilization, encapsulation, extrusion, homogenization, sonication, melting, solubilizing, evaporation, sterilization, filtration, irradiation, mixing, coating, size reduction, spraying, or a combination thereof.

19. The dosage form of claim 17, which comprises the pharmaceutical emulsion formulated as an injectable, a drink, an eye drop or spray, a nasal drop or spray, a buccal drop or spray, a cervical drop or spray, an inhalant, a lotion, a gel, a liniment, a cream, a paste, a solution, a suppository, an ovule, a wafer, a troche, a sachet, an elixir, a tineture, a douche, an aerosol, a patch, or a combination thereof.

20. The dosage form of claim 17, wherein the dosage form is adapted for parental, enteral, ocular, nasal, sublingual, buccal, topical, intra-cervical, rectal, intramuscular, intradermal, pulmonary, transmucosal, intra-thecal, intravenous, intra-arterial, epidural, intra-cavity, intra-organ transdermal, intra-lymphatic, intra-cranular, or intra-lumoral administration, or a combination thereof.

21. The pharmaceutical emulsion of claim 1, having a mean particle diameter of less than about 5 μm.

* * * * *